United States Patent
Breivogel et al.

(12)
(10) Patent No.: US 6,303,154 B1
(45) Date of Patent: Oct. 16, 2001

(54) CHEMICAL ALTERATION OF MAMMAL URINE AND MAMMAL BLOOD

(76) Inventors: Boris Breivogel; Horst Kief, both of Ludwigstrasse 30, Ludwigshafen (DE)

( * ) Notice: Subject to any disclaimer, the term of this patent is extended or adjusted under 35 U.S.C. 154(b) by 0 days.

(21) Appl. No.: 09/404,297

(22) Filed: Sep. 24, 1999

(51) Int. Cl.[7] .......................... A61K 35/12; A61K 35/24; A61K 35/37; A01N 37/18; A61M 15/02
(52) U.S. Cl. .......................... 424/545; 424/520; 424/537; 128/202.25; 514/885
(58) Field of Search .................................. 435/1, 2, 193.1, 435/529, 545, 269, 267, 262, 268; 424/278.1, 529, 545, 514, 520, 537; 514/885; 128/202.25

(56) References Cited

U.S. PATENT DOCUMENTS 5,052,382 * 10/1991 Wainwright et al. .
5,651,993 * 7/1997 Edelson et al. .

FOREIGN PATENT DOCUMENTS

| 195-12-027 | 10/1996 | (DE) . |
| 195 26 112A1 * | 1/1997 | (DE) . |
| 0265548A1 | 5/1988 | (EP) . |
| 0607593A2 | 7/1994 | (EP) . |

OTHER PUBLICATIONS

Partial Translation of EP 0607593A2.
Partial Translation of EP 0265548A1.

* cited by examiner

Primary Examiner—Christopher R. Tate
Assistant Examiner—Michele Flood
(74) Attorney, Agent, or Firm—Jacobson Holman, PLLC

(57) ABSTRACT

A method for chemical modification of mammal urine and mammal blood is disclosed.

20 Claims, No Drawings

CHEMICAL ALTERATION OF MAMMAL URINE AND MAMMAL BLOOD

FIELD OF THE INVENTION

This invention relates to methods for the chemical modification of mammal urine and mammal blood. The modified blood or the modified urine have immune modulatory effects when administered to a mammal and can be used for the treatment of immune discorders.

BACKGROUND OF THE INVENTION

Mammal blood is known to consist of a cellular and a non cellular fraction. The non cellular fraction in non hemolytic blood is called plasma, a watery solution of minerals and complex biochemical synthesis products such as proteins (derived mostly from the liver and in form of immuneglobulines from cells of the immune system), carbohydrates, proteoglycans etc.

The cellular phase can be separated by centifugation or spontaneous sedimentation of the blood cell components and yields mostly erythrocytes and thrombocytes and a smaller fraction of leukocytes. Those can be differentiated in granulocytes and lymphocytes. Newer research has turned especially to the subgroups of the lymphocytes through flow cytometry. After specific staining of surface antigens it has been possible to identify different groups of cells among these. Cells with CD4 were called T-Helper cells (inducing and increasing immune activity), CD8 Cells were called T supressor or cytotoxic cells (reducing and controlling immune activity). A further discrimination of T helper cells in Th1 and Th2 cells was possible. Th1 cells produce preferential proinflammatory cytokins like interleukin 2, interferon gamma and tumor necrosis factor. Th1 cells are used for the attack of intracellular target antigens and tumor cells by their cytotoxic activity. The action of Th2 cells is preferential anti-inflammatory, they are producing Interleukin (IL) 4, IL 10 and IL 13. Th2 cells are used for the control of extracellular antigens. By the interaction of the Th1, the Th2 and the antigen presenting cells, the effector action of the immune system is controlled. Interferon gamma echances the production of prionflammatory substances as tumor necrosis factor, IL 1, IL 6, IL 12oxygen radicals an NO. IL 4 is counteracting the proinflammatory activity of these substances. Different groups of diseases show typical shifts of the balance in favor of Th1 or Th2 cells. A shift in favor of the Th1 cells is considered positive for tumor patients (anti tumor activity) but noxious for patients with organ specific automimmune diseases (like rheumatoid arthritis, uveitis, thyreoiditis). A predominance of Th2 cells will be noxious for allergic disease (Eczema), immune globulin mediated diseases and sclerodermia. This is considered as a possible explanation for the fact, that patients with active allergies and neurodermatitis are less prone for cancer. The pathologic activity and overweight of parts of the immune system in patients with allergic skin or lung disease, rheumatic and other autoimmune disease as well as many types of cancer has led to search for complex immunemodulatory agents that can rebalance that causing unbalance to influence the resulting disease.

Mammal urine or alternatively ultrafiltrate of dialysis treatments contain a spectrum of proteins and proteoglycans and other substances that pass physiologically the kidney filter. The substances are complex and differ in size and biologic function. A lot of urine substances probably have a biologic effect, but the subcutaneous administration of sterile urine of the same host mammal has not shown mentionable effects on the cells of the immune system. The same applies to the addition of sterile urine to leukocyte cultures of the same individual, no remarkable immunemodulatory effect was observed.

U.S. Pat. No. 4,632,980 (Zee et al.) discloses a method for virus inactivation of blood and blood products comprising treatment with low levels of ozone. Atfer virus inactivation the blood components are further separated and it can be used for the intended purpose.

U.S. Pat. No. 4,684,521 (Edelson) discloses a method and system for externally treating blood. It comprises treatment of blood with UV radiation in the presence of a photoactive agent.

U.S. Pat. No. 4,748,120 (Wiesehahn) discloses a method for the treatment of biological compositions with psoralen derivatives under irradiation conditions.

BRIEF DESCRIPTION OF THE INVENTION

It has now been found that oxidation of blood and urine under special conditions yeild a reliable substance for the treatment of disorders of the immune system. In one embodiment the present invention provides a method for chemical modification of mammal urine comprising the steps of collecting urine from a mammal, treating said mammal urine with an oxidizing agent and a gas atomosphere of at least 90% to 100% (v/v) oxygen in a container, adding at least one protease, removing substances with a low molecular weight to yield a modified mammal urine.

In a second embodiment the present invention provides a method for chemical modification of mammal blood comprising the steps of collecting blood from a mammal, separating the blood in a plasma phase and a cell phase, treating of the plasma phase, the cell phase or both with an oxidizing agent and a gas atmosphere of about 90% to 100% (v/v) oxygen in a container, combining the plasma phase with the cell phase, adding a cell culture medium and at least one protease, adding modified mammal urine prepared according to the first embodiment, incubating for 16 to 36 hours at about 37° C., adding a preservation agent to yield modified mammal blood.

In a third embodiment the invention provides a method of treating immune disorders comprising the step of administering to a patient in need thereof modified mammal urine prepared according to the method of the invention.

In a fourth embodiment the invention provides a method of treating immume disorders comprising the step of administering to a patient in need thereof modified mammal blood prepared according to the method of the invention.

In a fifth embodiment the present invention provides the substance being able to modulate the immune system.

DETAILED DESCRIPTION OF THE INVENTION

The first embodiment of the present invention discloses a method for the chemical modification of mammal urine. This method comprises the step of collecting urine from mammal. It is preferred that the collection is perfomed in a way to enable sterile collection of the urine. This can be done by sterile cathederization of the urinary bladder or collection of midstream urine. To keep the urine sterile a sterile container should be used, e.g. a disposable sterile plastic container. Depending on the presence of non soluble components in the urine the urine can be centrifuged and the sediment may be discarded. Conventional test methods for the screening of bacterial contaminations, are e.g. sticks test on nitrite.

The collected mammal urine is now treated with an oxidizing agent at a gas atmosphere of at least about 90% (v/v) oxygen. The term "oxygen" is meant to comprise the element oxygen in atomic and molecular pure forms, especially in the form of $O_2$ and $O_3$. $O_2$ is the main component of the gas atmosphere. As oxidizing agents $H_2O_2$ and $O_3$ are especially preferred. $H_2O_2$ may be added as a diluted solution to the urine. Suitable amounts are in the range of 1 to 3 ml of a one percent solution of $H_2O_2$ per 100 ml of urine. The ozone ($O_3$) may be added to the gas atmosphere.

If ozone is used as an oxidizing agent it should be present in a concentration of about 50 to 100 $\mu$g/ml of the oxygen atmosphere. Apparatus for the generation of ozone are commercially available and are described, e.g. in U.S. Pat. No. 5,052,382 to Waenright and U.S. Pat. No. 5,053,140 to Horste, both incorporated by reference. It is of high importance to perform the oxidation in a gas atmosphere having a concentration of at least 90% (v/v) of $O_2$. The inventors of the present invention have revealed that this combination of weak oxidizing $O_2$ with a strong oxidizing agent allows a reliable and reproducible modification of mammal urine. It is preferred that the $O_2$ concentration in the gas atmosphere is as high as possible, preferably at least 95% and more preferably at least 99%. It is most preferred that the concentration of $O_2$ is as high as commercially available. The only relevant other gas may be ozone in the case that ozone is used as an oxidizing agent. The oxygen should be of medical grade to avoid contaminations of the urine. The oxygen atmosphere in the container is obtained by removing the air atmosphere above the urine in the container or use of an evacuated container and addition of the $O_2$ atmosphere. The $O_2$ atmosphere may have a pressure in the range of less than atmospheric pressure up to about 1 bar above atmospheric pressure. It is preferred that the pressure in the container is close to atmospheric pressure because this facilitates handling and avoids complicated mechanisms for tight sealing of the container. It is preferred to provide intimate contact between the oxygen atmosphere and the urine. A suitable method is shaking of the urine with the oxygen atmosphere to allow reaction between the urine, the oxidizing agent and the oxygen atmoshere. The concentration of the oxidizing agent may be varied in a broad range which influences certainly the reaction velocity of the oxidizing agent. Suitable concentrations of the oxidizing agent are in a range of 1 to 5 $\mu$mole per ml urine. It is obvious for a person skilled in the art that the oxidizing agent should not incorporate any toxic substances into the urine. To allow intimate mixture of the gas atmosphere with the urine it is preferred that the volume of the gas atmosphere is at least 50% of the volume of the urine. Preferably, it is in the range of 50 to 200% of the volume of the urine and more preferably of about the same volume as the urine.

After adding the oxidizing agent at least one protease must added. Suitble proteases comprise serine proteases such as papaine, trpysine, chymotrypsine, mixtures thereof and the like. The enzymatic activity should be in the range of 0.1 to 2 microkat per milliliter of urine. One kat is defined as the amount of an enzyme cutting one mole of peptide bonds per second. After the addition of the oxidizing agent and the at least one protease the urine is incubated in the dark in a range of 2 to 18 hours at a temperature of preferably 37° C. Lower temperatures may be used but this may require increasing the amount of oxidizing agent and the amount of proteases or extending the incubation time because the reaction velocity depends on the temperature and the concentration of the reagents. Slightly higher temperatures may also be used but substantially higher tempertures may denature sensitive components of the urine and may decrease the effecicency of the modified urine.

After the incubation, substances with a low molecular weight should be removed. The term "substances with a low molecular weight" is used to define substances having a molecular weight below about 6,000 Dalton, more preferably below about 5,000 Dalton. A preferred method for the removal is the use of an ultrafiltration unit. Suitable ultrafiltration membranes are, e.g. Ultrafree-15-Biomac5K (commercially available from Milipore Inc. The ultrafiltration can be conveniently performed with the aid of a centrifuge which speeds up the process of ultrafiltration. Ultrafiltration furthermore reduces the amount of water in the urine thus increases the concentration of the high molecular weight components. Instead of ultrafiltration other methods can be used. As suitable method is e.g. gel filtration. After the removal of the low molecular weight susbtances and optionally water, the modified mammal urine is preferably treated again with an oxidizing agent and a gas atmosphere as described above. This repeated treatment increases the share of the components which are modified by the method of the present invention and thus increases the effectiveness of the treatment. The obtained modified mamal urine should be stored below 4° C. or may be frozen.

As a further embodiment the present invention discloses a method for chemical modification of mammal blood comprising treating the blood with the modified mammal urine prepared according to the first embodiment. The method comprises the step of collecting blood from a mammal. This blood is collected in the usual medical way and is transferred into the container comprising heparine to aviod clotting of the blood. 6,000 IU sterile sodium heparine (volume 2 to 5 ml) or the equivalent amount of low molecular heparine are sufficient for about 200 ml blood. Alternatively, a bone marrow aspirate or homogenized tissue containing leukocytes can be used. As described above sterile conditions should be met during collecting and further processing of the blood. Laminar flow conditions are preferably used during further processing. A sample of the collected blood is checked for HIV, hepatitis B and C in the usual way to warrant safety of the laboratory personal.

The blood is then separated in a plasma phase and a cell phase. This can be done by centrifugation at approximately 750 g or alternatively by allowing the cell compartment (comprising erythrocytes, thrombocytes and leukocytes) to sediment in the container.

After spearation of the cell phase and the plasma phase into containers the plasma phase, the cell phase or both are treated with an oxidizing agent and a gas atmosphere of at least 90% (v/v) oxygen. The description of the oxidation step above equally apply to the treatment of the plasma phase and the cell phase.

Without wishing to be bound to a theory it is believed that the leukocytes proliferate as a result of the treatment with the oxidizing conditions or increase production of immunogenic products. To enable proliferation, a cell culture medium is added which comprises salts and amino acids as routinely used in cell culture. Suitable media are commerically available. A preferred, but not limiting example of a cell culture medium is described in the examples. A 4.2% (v/v) $NaHCO_3$ solution can be added to adjust the pH. Furthermore, a suitble amount of at least one protease is added. Suitable proteases and amounts are explained above.

Thereafter, modified mammal urine prepared according to the first embodiment of the invention, preferably from the same mammal is added. This mixture is incubated for about of 16 to 36 hours at about 30° C. in the darkness. A coventional role mixer or shaker can be used. Significantly higher or lower temperature conditions would strongly influence the proliferation efficiency of the cells. It is, therefor, considered important to keep the temperature in the range form 35 to 40° C. It is belived that under this conditions the cells start to proliferate or produce a disease specific substance pattern. It is believed that the leukocytes of a person with an immune disorder contain specific information for the production of a specific remedy or for the production of the remedy inducing function if administered to the donor of the leukocytes for this disorder. After the incubation a suitable preservation agent is added. A number of preservation agents for the presevation of blood are known. Suitable solutions are known under the abbreviatons ACD (anticoagulant citrate/dextrose solution) and CPD (anticoagulant citrate phosphate dextrose solution). These solutions comprise a citrate puffer system, glucose and optionally a sodium phosphate salt. These preservation agents have a weak acidic pH between 4 and 6. A suitable preservative premix is ACD stabilizator Fon A commercially available from Fresenius, Germany.

The modified urine and the modified blood of the present invention may be used for treating immune disorders. Allergic diseases, rheumatic diseases, autoimmune diseases and immune deficient diseases can be successfully treated or at least be improved by this treatments. Allergic diseases include e.g. Hay fever (rhinoconjuctivitis allergica, allergic asthma, neurodermitis (Eczema) etc. Rheumatic diseases include e.g. chronic polyarthritis, systemic lupus erythermatodes etc. Other autommimune diseases include immune vasculites, immune nephritis etc. Immune deficiencies include e.g. acquired immune deficiencies, chronic virus infections. Before administration the person skilled in the art would be aware that it is necessary to check the modified urine or the modified blood for sterility and absence of endotoxins. Suitable tests comprise conventional medical urine in cultures, e.g. uricult or conventional medical blood culture. Absence of endotoxins can be checked with Limulus Amebocyte Lysate Test (BioWhitakker Inc., Walkersville, USA). The substances prepared according to the method of the invention can be administered orally, transdermally, by inhalation or parentally. It is preferred that the modified blood or the modified urine are prepared from the urine or the blood of the patient to be treated with the modified urine or the modified blood.

In a further embodiment the present invention provides substances which have an immune modulatory effect. Treating of urine from patients with, e.g. severe allergic diseases show the disappearance of two peaks and the appearance of two new peaks. This effect is not seen in healthy individuals. It is believed that these new isolated substances can be isolated and may be successfully used as immune modulatory substances.

Experimental

Modification of mammal urine 200 ml urine of one mammal host are sampled in a sterile plastic container in the usual medical way to obtain sterile urine. A usual stix test on nitrite is used to screen for severe bacterial contaminations. 4 portions of 50 ml are centrifuged at 20° Celsius to 2000 times gravity. The clear solution above the sediment is drawn into a sterile syringe and transferred through a sterile bacteria filter (0.2 micrometer, e.g. from Millipore) into a sterile, evacuated glass bottle of 500 ml volume. The remaining sediment is checked microscopically for bacteria. A gas atmosphere of 100 percent oxygen with an $O_3$ content of 75 microgram per ml $O_2$ is produced in a suitable apparatus and administered under constant manual shaking into the evacuated bottle through the urine until the vacuum is equalized. Alternatively instead of a mixed Ozone/Oxygen atmosphere pure oxygen can be administered after adding 2 ml of a 1% solution of $H_2O_2$ Subsequently, 1 ml mixed sterile enzyme solution (comprising 3 mg Papaine—equivalent 8 F.I.P.E, 1.5 mg Trypsin—equivalent 1.1 microkat, 2 mg Chymotrypsine—equivalent 10 microkat, total proteolytic activity of 64 F.I.P.E according to Papaine method) per 20 ml urine is added into the bottle. The mixture with the oxygen ozone or pure oxygen atmosphere is incubated upright and dark at 37° Celsius for 2–18 hours. After incubation, aliquots of 10 ml of the treated urine are centrifuged in a concentrator filter that will preserve all particles greater 5000 Dalton. (e.g. ultrafree-15 biomax-5 k) at 20° Celsius at 3000 times gravity (solution "A").

This process reduces the amount of liquid by about 50%. Solution "A" is filtered through a sterile filter (millipore, 0.2 micrometer) into another clean sterile evacuated bottle. Again a gas atmosphere of 100 percent oxygen with an $O_3$ content of 75 microgram per ml $O_2$ is produced in a suitable apparatus (Alternatively instead of a mixed Ozone/Oxygen atmosphere pure oxygen can be administered after adding 2 ml of a 1% solution of $H_2O_2$ under constant shaking through the urine and administered under constant manual shaking into the evacuated bottle through the urine until the vacuum is equalized. 2 ml of the solution undergo a conventional medical urine culture (e.g. uricult) to prove sterility. Another sample undergoes limulus amebocyte lysate Test (Bio Whitakker Inc, Walkersville, USA) to warrant absence of endotoxines. After passing these test, the solution can either be used for further isolation of the contained biological active substances or be used as a complex agent, to modulate the immune activity of a patient.

Identification of process products

HPLC analysis of human urine sample before and after the above described procedures show a vanishing of two peaks with a retention time of 25.0 and 33.5 minutes in the modified urine. Two new peaks show up at 19.8 and 20.6 minutes post start. Both are double peaks and reproducible. A reducing treatment with dithiotreitol, to reveal disulfide bonds was not able to alter the substances that created those peaks. Control urine HPLC of healthy adults of both sexes showed the peak at 33.5 minutes but no peaks at 19.8, 20.6 and 25.0 minutes. This provides a possibility to define the successful modification of the urine.

Clinical results

The repetitive oral or subcutaneous administration in increasing dosage of sterile 1:10000 to 1:10 dilutions in physiologic saline of the product have shown drastic remissions in children and adults with a topic eczema (neurodermatitis). Several cases have been documented.

Modification of mammal blood

Step 1: A sterile, prior evacuated glass bottle of 250 ml total volume (usual type suitable for infusion of medical solutions) is filled with 6000 IU sterile sodium heparin (volume 2–5 ml) or the equivalent amount of low molecular heparin to aviod later blood clotting.

200 ml blood of one mammal host are sampled into the bottle in the usual medical way to obtain sterile blood.

All further steps must be carried out under sterile conditions and laminar flow to aviod contamination.

Step 2: 7–9 ml blood are used to be checked for antibodies against HIV, hepatitis B and C in the usual medical state of the art way. (To warrant safety for the laboratory personal). The remaining blood volume is reduced to 120 ml by removing blood.

Step 3: By centrifugation of the bottle for 20 minutes 750 times gravity at 20° Celsius a separation of plasma (above) and cell compartment (erythrocytes, thrombocytes, leukocytes-below) is obtained.

Step 4: The plasma above the visual distinct cell compartment is removed by suction from the original bottle (called here "cell bottle") into another sterile evacuated glass bottle of about 250 ml volume. (called here: "plasma bottle")

In Step 5, the remaining vacuum in the plasma bottle is equilibrated by administering a gas atmosphere of 100 percent oxygen with an $O_3$ content of 40–60 microgram per ml O2 (produced in a suitable apparatus as above mentioned) which is administered under constant manual shaking into the evacuated bottle through the plasma until the vacuum of the bottle is equalized. Alternatively instead of a mixed Ozone/Oxygen atmosphere pure oxygen can be administered after adding 1 ml of a 1% solution of $H_2O_2$ under constant shaking through the liqid.

Step 6: The plasma (plasma bottle) is combined with the residual blood cell sediments (cell bottle) and mixed by soft shaking.

Step 7: Per 100 ml content of the glass bottle the stated amounts of the following solutions are added and mixed: 30 ml of a premixed cell culture medium is added comprising:

| 350 ml contain | |
|---|---|
| calcium chloride*2- $H_2O$ | 0.368 g |
| sodium chloride | 8.182 g |
| Potassium chloride | 0.373 g |
| magnesium chloride*6-$H_2O$ | 0.305 g |
| glucose | 1 g |
| alanine | 0.48 g |
| arginine | 0.339 g |
| aspartinic acid | 0.102 g |
| glutaminic acid | 0.168 g |
| $N_2$-glycyl-L-tyrosine | 0.1035 g |
| histindine | 0.204 g |
| isoleucine | 0.168 g |
| leucine | 0.237 g |
| lysin acetate | 0.381 g |
| methionine | 0.168 g |
| phenylalanin | 0.1755 g |
| proline | 0.204 g |
| serine | 0.135 g |
| threonine | 0.168 g |
| tryptophane | 0.057 g |
| valine | 0.219 g |
| phytomenadion | 0.020 g |
| retinolpalmitate | 0.00033 g |
| thiamin hydrochlorid | 0.002 g |
| riboflavin-5-phosphate | 0.002 g |
| nicotinamid | 0.008 g |
| dexpanthenol | 0.005 g |
| pyridoxin hydrochlorid | 0.003 g |
| ascorbic acid | 0.02 g |

-continued

| | |
|---|---|
| DL-alpha-tocopherolacetate | 0.001 g |
| sterile water 350 ml | | plus 15 ml sterile 4.2% $NaHCO_3$ solution plus 2 ml mixed sterile enyzme solution (see above).

Alternatively, the cell phase can be treated:

Alternative step 5: the remaining vacuum in the cell bottle is equilibrated by administering a gas atmosphere of 100 percent oxygen with a n $O_3$ content of 6 –12 microgram per ml $O_2$ (produced in a suitable apparatus) which is administered under constant manual shaking into the evacuated bottle through the cell enriched liquid until the vacuum of the bottle is equalized. Alternatively instead of a mixed Ozone/Oxygen atmosphere pure oxygen can be administered after adding 1 ml of a 0.1% solution of $H_2O_2$ under constant shaking through the liquid. Alternative step 6a: 2 ml mixed sterile enzyme solution (see above) are added to the plasma bottle.

Alternative step 6b: The so altered plasma is incubated for 1–2 hours at 37° Celsius under constant shaking and then combined with the cell bottle and mixed by soft shaking. ("common" bottle)

Alternative step 7: Per 100 ml content of the "common" bottle 20 ml of the premixed cell culture medium (see above) is added.

Step 8: Within the next 4 hours of incubation on a constant roller device 5 ml of the modified urine of the example are added per 100 ml bottle content.

Step 9: The now complete cell culture is incubated for 16–36 hours on a rollmixer or shaker at 37° Celsius in the dark.

Step 10: Per 100 ml content in the incubating bottle 15 ml of ACD Stablisator Fon A glucose (comprising *1$H_2O$ 23.9 g, citric acid* 1$H_2O$ 7.9 g, sodium citrate*2$H_2O$ 21.8 g, fill up with water to a volume of 1 liter) is added. 2 ml of the solution undergo a conventional medical blood culture to prove sterility. Another sample undergoes limulus amebocyte lysate Test (Bio Whittaker Inc, Walkersville USA) to warrant absence of endotoxines. The solution must be stored at maximum 4° Celsius or be shock frozen to preserve efficacy. It can be used, to isolate and study the altered biologic substances or on an empiric base be administered orally, transdermally, by inhalation or parenterally to achieve an immunemodulatory effect in disorders of the immune system.

Clinical results

The repetitive oral or subcutaneous administration in increasing dosage of sterile 1:10000 to 1:10 dilutions in physiologic saline of the product have shown drastic and long term remissions in children and adults with atopic eczema (neurodermatitis) and other diseases related to similar immune disorders. More than 801 cases have been long term documented, showing statistically significant improval.

What is claimed is:

1. A method for chemical modification of mammal urine comprising the step of colltecting urine from a mammal, treating said mammal urine with an oxidizing agent and a gas atmosphere of about 90% to 100% (v/v) oxygen in a container, adding at least one protease and incubating for a sufficent time, removing substances with a low molecular weight to yield a modified urine.

2. The method according to claim 1, wherein the mammal is a human being.

3. The method according to claim 1, wherein the oxidizing agent is selected from the group consisting of $H_2O_2$, $O_3$, and combinations thereof.

4. The method according to claim 1, wherein the oxidizing agent is used at a concentration of 1 to 5 micromole per milliliter of the mammal urine.

5. The method according to claim 1, wherein the volume of the gas atmosphere is at least 50% of the volume of the mammal urine.

6. The method according to claim 1, wherein the gas atmosphere has a pressure of 0 to 1 bar above atmospheric pressure.

7. The method according to claim 1, wherein the gas atmosphere has at least 95% (v/v) oxygen.

8. The method according to claim 1, wherein the gas atmosphere has at least 99% (v/v) oxygen.

9. The method according to claim 1, wherein the at least one protease is selected from the group consisting of papain, trypsin, chymotrysin, and mixtures thereof.

10. The method according to claim 1, wherein the at least one protease has an enzymatic activity in the range of 0.1 to 2 microkat per milliliter of the mammal urine.

11. The method according to claim 1, wherein ultrafiltration is used for removing substances with a molecular weight below 5,000 Dalton.

12. The method according to claim 1, further comprising th step of, after removing the substances with a low molecular weight, treating the modified urine with an oxidizing agent and a gas atmosphere of about 90% to 100% (v/v) oxygen in a container.

13. The method according to claim 11, wherein the modified urine is diluted in logarithmic steps with a sterile isotonic solution.

14. The method according to claim 11, wherein the substances with a low molecular weight are substances having a molecular weight below about 5,000 Dalton.

15. A method of treating immune disorders comprising the step of administering to a patient in need thereof modified mammal urine prepared according to a method comprising the steps of collecting urine from a mammal, treating said mammal urine with an oxidizing agent and a gas atmosphere of about 90% to 100% (v/v) oxygen in a container, adding at least one protease and incubating for a sufficent time, removing substances with a low molecular weight to yield the modified mammal urine.

16. The method according to claim 15, wherein the mammal from whom the urine is collected is the patient.

17. The method according to claim 15, wherein the disorder of the immune system is selected from the group consisting of allergic diseases, rheumatic diseases, autoimmune diseases, and immune deficiencies.

18. The method according to claim 15, wherein the mammal from whom the urine is collected is the patient.

19. The method according to clain 15, wherein the disorder of the immune system is selected from the group consisting of allergic diseases, rheumatic diseases, automimmune diseases, and immune deficiencies.

20. Modified mammal urine prepared according to claim 1.

* * * * *